US010980357B2

(12) United States Patent
Burnside et al.

(10) Patent No.: US 10,980,357 B2
(45) Date of Patent: Apr. 20, 2021

(54) DIAPER CHANGING ASSISTANCE DEVICE

(71) Applicants: Charlie Burnside, Kent, WA (US);
Karen Burnside, Kent, WA (US)

(72) Inventors: Charlie Burnside, Kent, WA (US);
Karen Burnside, Kent, WA (US)

( * ) Notice: Subject to any disclaimer, the term of this patent is extended or adjusted under 35 U.S.C. 154(b) by 356 days.

(21) Appl. No.: 15/942,698

(22) Filed: Apr. 2, 2018

(65) Prior Publication Data
US 2018/0279802 A1    Oct. 4, 2018

Related U.S. Application Data

(60) Provisional application No. 62/479,893, filed on Mar. 31, 2017.

(51) Int. Cl.
*A61F 5/37* (2006.01)
*A47D 15/00* (2006.01)
*A61B 90/00* (2016.01)
*A47D 5/00* (2006.01)

(52) U.S. Cl.
CPC ............ *A47D 15/005* (2013.01); *A61B 90/05* (2016.02); *A61F 5/3715* (2013.01); *A47D 5/00* (2013.01)

(58) Field of Classification Search
CPC .... A47D 15/00; A47D 15/005; A47D 15/008; A47D 5/00; A47D 5/006; A47D 5/004; A47D 13/08; A61B 90/05; A61F 5/37; A61F 5/3761; A61F 5/3769; A61F 5/3715; A61F 5/0193; A61F 5/01; A61F 5/3723; A63B 69/0062; A63B 69/0059; A63B 69/0057; A63B 69/3608; E05B 75/00

USPC ............. 128/869, 882, 846, 876, 878, 879; 446/71, 81, 227; 5/655, 648, 650, 603, 5/424, 513, 652; 297/464, 466; 119/816
See application file for complete search history.

(56) References Cited

U.S. PATENT DOCUMENTS

| | | | | |
|---|---|---|---|---|
| 4,186,688 A * | 2/1980 | Gaitan | ................... | A01K 15/04 |
| | | | | 119/712 |
| 4,205,669 A * | 6/1980 | Hamann | .................. | A47D 5/00 |
| | | | | 5/424 |
| 5,038,799 A * | 8/1991 | Fowler | .................. | A61F 5/3761 |
| | | | | 128/878 |
| 5,799,654 A * | 9/1998 | Kassan | ................. | A61F 5/3715 |
| | | | | 128/869 |
| 6,149,489 A * | 11/2000 | Johnson | ................. | A47D 13/02 |
| | | | | 297/183.1 |
| 6,254,561 B1 * | 7/2001 | Borden | ................ | A61N 5/1049 |
| | | | | 128/845 |
| 6,585,672 B1 * | 7/2003 | Crompton | ............. | A61F 5/0193 |
| | | | | 128/869 |
| 7,178,877 B2 | 2/2007 | Watson | | |
| 8,833,310 B2 * | 9/2014 | Konigsberg | ......... | A01K 27/003 |
| | | | | 119/770 |
| 2005/0235424 A1 | 10/2005 | Waite | | |
| 2006/0075794 A1* | 4/2006 | Ling | ................... | E05B 73/0005 |
| | | | | 70/58 |

(Continued)

*Primary Examiner* — Victoria J Hicks
(74) *Attorney, Agent, or Firm* — Boudwin Intellectual Property; Daniel Boudwin

(57) ABSTRACT

A diaper changing assistance device. The diaper changing assistance device provides efficiency to a parent changing a diaper of an infant. A rod is attached between an infant's ankles by a pair of ringed members. The rod can be freely lifted by the parent so that the parent is able to change the diaper of the infant with reducing flailing and movement of the infant.

13 Claims, 6 Drawing Sheets

(56) References Cited

U.S. PATENT DOCUMENTS

| | | |
|---|---|---|
| 2011/0209716 A1 | 9/2011 | Scarsbrook |
| 2014/0013513 A1 | 1/2014 | Simental |
| 2014/0101857 A1 | 4/2014 | Hanson |
| 2014/0272858 A1* | 9/2014 | Fattori ................ A63B 69/18 |
| | | 434/253 |

* cited by examiner

DIAPER CHANGING ASSISTANCE DEVICE

CROSS REFERENCE TO RELATED APPLICATIONS

This application claims the benefit of U.S. Provisional Application No. 62/479,893 filed on Mar. 31, 2017. The above identified patent application is herein incorporated by reference in its entirety to provide continuity of disclosure.

BACKGROUND OF THE INVENTION

The present invention relates to a diaper changing assistance device. Changing an infant's diaper is a challenging task for many parents. Because of how diapers are packaged and because of how active infants can be, a parent must normally hold an infant's legs while simultaneously applying the diaper. Furthermore, Infants frequently flail their legs, making the diaper changing process more difficult. In addition to these difficulties and the amount of time that the diaper changing process can take, an unpleasant mess can be created that will require even more time and effort to clean up.

Because of the lack of such a device in the known art, there is a need for a diaper changing assistance device that provides parents with the ability to change their infant child's diaper in a safe and efficient manner.

SUMMARY OF THE INVENTION

In view of the foregoing disadvantages inherent in the known types of diaper changing assistance devices now present in the known art, the present invention provides a diaper changing assistance device wherein the same can be utilized for providing convenience for the user when changing a diaper of an infant.

The present system comprises an elongated rod that has a first end and a second end. Each end has a ringed member affixed thereon. The ringed members are securable around themselves by a fastener disposed on each of the pair of ringed members.

It is therefore an object of the present invention to provide a new and improved diaper changing assistance device that has all the advantages of the known art and none of the disadvantages.

Another object of the present invention is to provide a housing that is securable to the elongated rod such that supplies for the diaper changing process can be stored therein.

A further object of the present invention is to provide a clear shield configured to repel fluids projected from an infant during the diaper changing process.

Yet another object of the present invention is to provide an elongated rod that is adjustable such that the rod will be usable with any infant while ensuring the comfortability of said infant.

Still yet another object of the present invention is to provide a light mechanism configured to distract the infant during the diaper changing process.

A further object of the present invention is to provide an audio mechanism designed to comfort and distract the infant during the diaper changing process.

Yet another object of the present invention is to provide a pair of ringed members that are rotatably attached to the first end and the second end of the elongated rod, such as to provide additional comfort to the infant.

Still yet another object of the present invention is to provide a padding material disposed on an interior surface of each of the ringed members such as to provide additional comfort to the infant.

A further object of the present invention is to provide a diaper changing assistance device having hook and loop fasteners such as to securely hold the legs of an infant during the diaper changing process.

Yet a further object of the present invention is to provide a diaper changing assistance device having snap clasp fasteners such as to securely hold the legs of an infant during the diaper changing process.

Still yet another object of the present invention is to provide a quick release button configured to release the fasteners of the diaper changing assistance device such as to enable a parent or guardian to quickly release the fastener and remove the diaper changing assistance device if needed.

Other objects, features and advantages of the present invention will become apparent from the following detailed description taken in conjunction with the accompanying drawings.

BRIEF DESCRIPTION OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
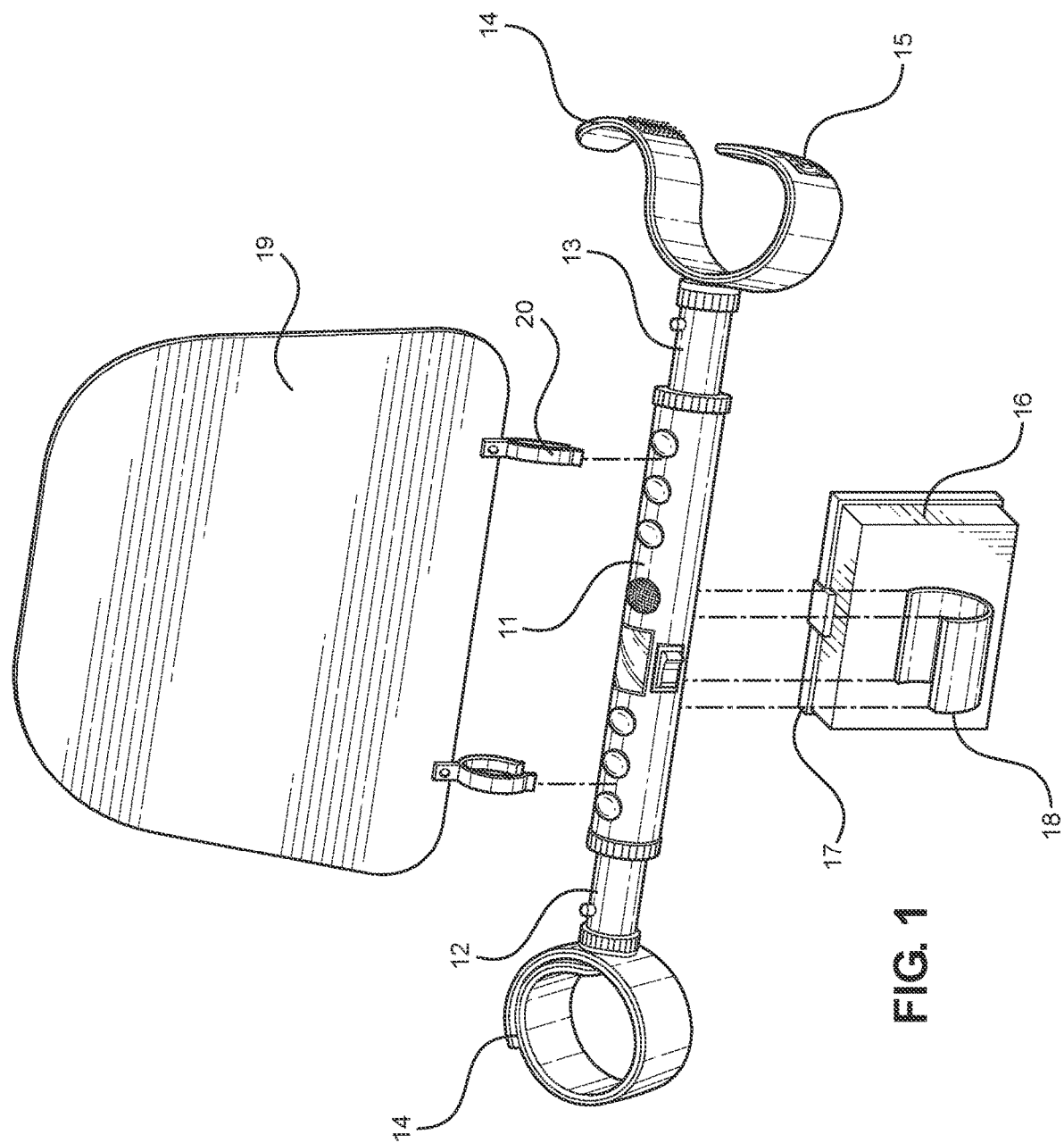
FIG. 1 shows an exploded view of an embodiment of the diaper changing assistance device.

Reference is made herein to the attached drawings. Like reference numerals are used throughout the drawings to depict like or similar elements of the diaper changing assistance device. The figures are intended for representative purposes only and should not be considered to be limiting in any respect.

Referring now to FIG. 1, there is shown an exploded view of an embodiment of the diaper changing assistance device. The diaper changing assistance device 10 comprises an elongated rod 11 having a first end 12 opposite of a second end 13. A pair of ringed members 14 is disposed on each of the first end 12 and the second end 13. Each ringed member of the pair of ringed members 14 comprises a fastener 15 disposed thereon. In the illustrated embodiment, the fastener 15 is a hook and loop fastener. The hook and loop fastener is movable between an engaged position, as illustrated on the first end 12 in the illustrated embodiment, and a non-engaged position, as illustrated on the second end 13 in the illustrated embodiment.

In one embodiment, the diaper changing assistance device further comprises a housing 16 disposed thereon. The housing 16 has a plurality of side walls wherein the plurality of side walls defines an internal cavity. In a further embodiment, the housing 16 defines a hingeably movable cover 17 configured to provide access to the internal cavity. In yet another embodiment, the housing 16 is configured to receive an object, such as a container of wipes or a packaged diaper therein. The hingeably movable cover 17 is adapted to provide an access point to the internal cavity.

Furthermore, a clip 18 is disposed on an external surface of the housing 16. The clip 18 is configured to enable removably attachment of the housing 16 to the elongated rod 11. In the shown embodiment, the clip 18 comprises a clasping unit configured to frictionally secure the housing 16 to the elongated rod 11. In an alternative embodiment, the clip 18 is disposed on the elongated rod 11 and comprises a receptor for the housing 16.

In another embodiment, the diaper changing assistance device 10 further comprises a transparent planar member 19. The transparent planar member 19 is configured to provide a protective barrier to a user from bodily fluids that are ejected from an infant upon which the diaper changing assistance device is mounted. The transparent planar member 19 is further configured to enable the user to see therethrough to allow the user to change a diaper while being protected by the transparent planar member 19. The transparent planar member 19 is made of any material that is both transparent and water-resistant.

The transparent planar member 19 further comprises a plurality of connectors 20 disposed on a bottom end thereof. The plurality of connectors 20 is configured to provide a mechanism by which the transparent planar member 19 is removably attachable to the elongated rod 11. In the shown embodiment, each connector of the plurality of connectors 20 comprises a clasping unit configured to frictionally secure the transparent planar member 19 to the elongated rod 11. Furthermore, the plurality of connectors 20 is configured to enable a user to freely rotate the transparent planar member 19 around the elongated rod 11. In an alternative embodiment, the plurality of connectors 20 is disposed on the elongated rod 11 and is configured to act as a receptor for the transparent planar member 19.

Figure 2:
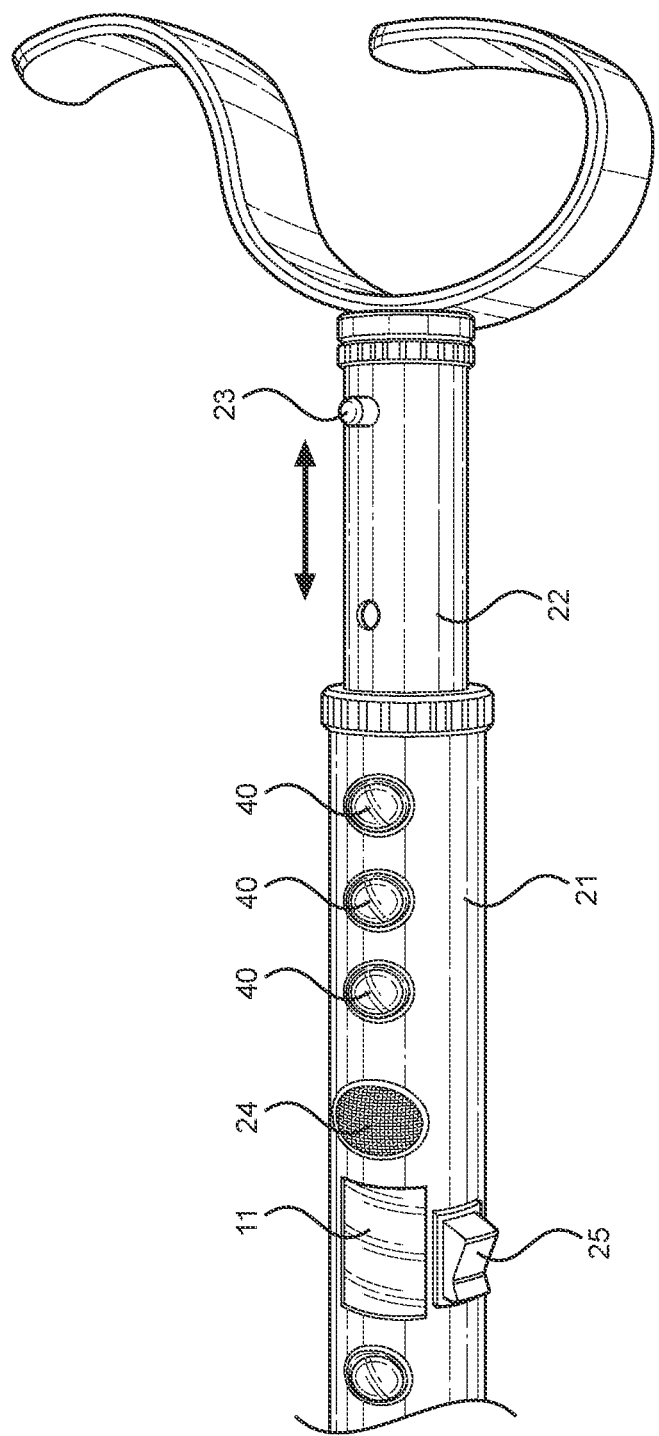
FIG. 2 shows a close-up view of the second end of an embodiment of the diaper changing assistance device.

Referring now to FIG. 2, there is shown a close-up view of the second end of an embodiment of the diaper changing assistance device. In one embodiment, the elongated rod 11 is comprised of a first rod member 21 and a second rod member 22. The first rod member 21 is hollow. Under this embodiment, the second rod member 22 is slidably insertable into the first rod member 21. Furthermore, the second rod member 22 comprises a tab 23. The tab 23 corresponds to a plurality of apertures disposed on the internal surface of the first rod member 21. Depression of the tab 23 will enable the user to adjust the length of the elongated rod 11 between the apertures of the plurality of apertures.

In another embodiment, the diaper changing assistance device further comprises an audio mechanism. The audio mechanism is configured to provide music to the infant secured in the device when the audio mechanism is engaged by the user. The audio mechanism comprises a speaker 24 configured to release sound therefrom. The speaker 24 is operably connected to an audio file storage device. The audio file storage device is configured to store audio files thereon. A control switch 25 is operably connected to an audio file storage device. The control switch 25 is configured to be engaged by the user, wherein engagement by the user will activate the audio file storage device. An audio file stored on the audio file storage device will be relayed through the speaker 24.

In another embodiment, a plurality of decorative lights 40 is disposed on the external surface of the elongated rod 11. In yet another embodiment, the plurality of decorative lights 40 is operably connected to the audio mechanism, such that the decorative lights 40 will flash when the audio file is played through the speaker 24.

Figure 3:
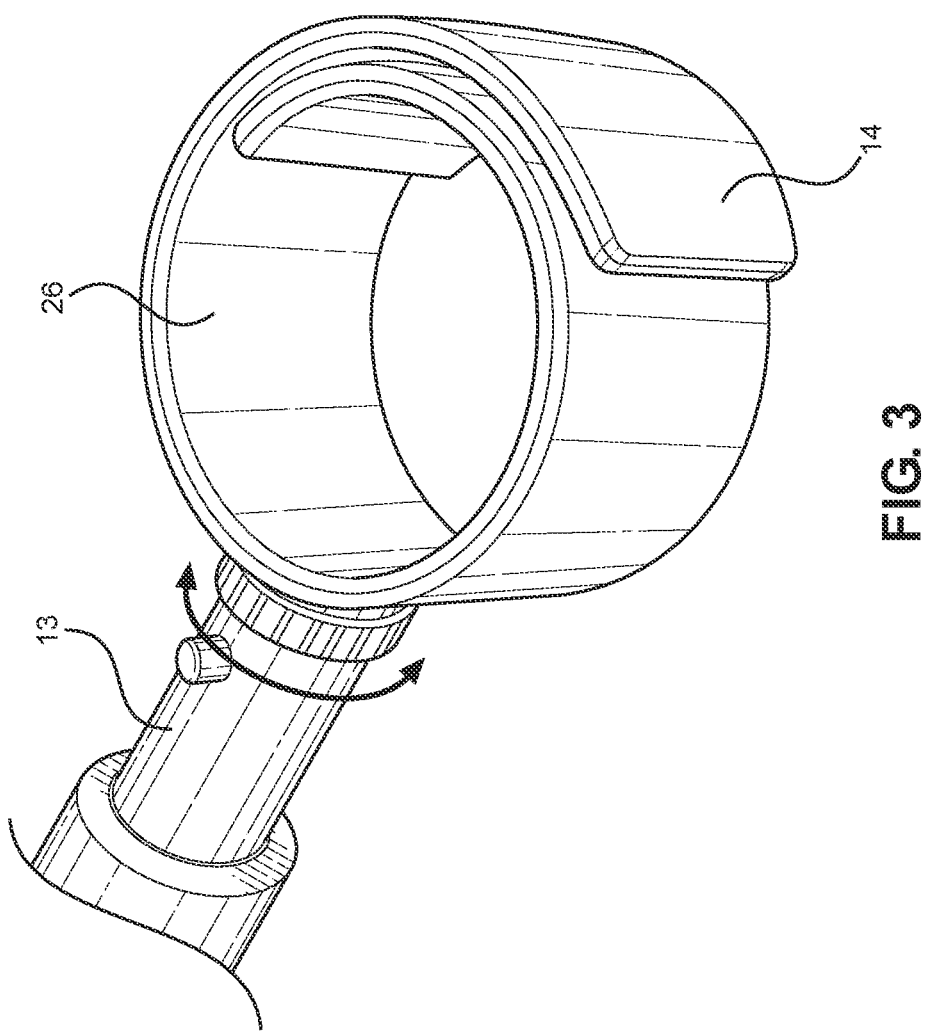
FIG. 3 shows a close-up view of a ringed member of an embodiment of the diaper changing assistance device.

Referring now to FIG. 3, there is shown a close-up view of a ringed member of an embodiment of the diaper changing assistance device. In one embodiment, the pair of ringed members 14 are rotatably attached to each of the first end and the second end 13 of the elongated rod. Rotatable attachment of each ringed member 14 will enable a more comfortable configuration for the infant secured in the device. Furthermore, rotatable attachment of each ringed member 14 will prevent any discomfort or bruising to the infant that may occur where the ringed members are not rotatably attached. In one embodiment, the ringed members 14 are independently rotatable. In another embodiment, the ringed members 14 are lockable into a specified location. The ringed members 14 are set apart at a user-specified distance, such that enough space is provided to remove a diaper, while not so far apart as to cause discomfort to the infant.

In another embodiment, each ringed member of the pair of ringed members 14 comprises a padding material 26 disposed on an internal surface thereof. The padding material 26 is configured to provide a comfortable surface along the portion of the ringed member 14 that is in contact with the infant secured therein.

Figure 4:
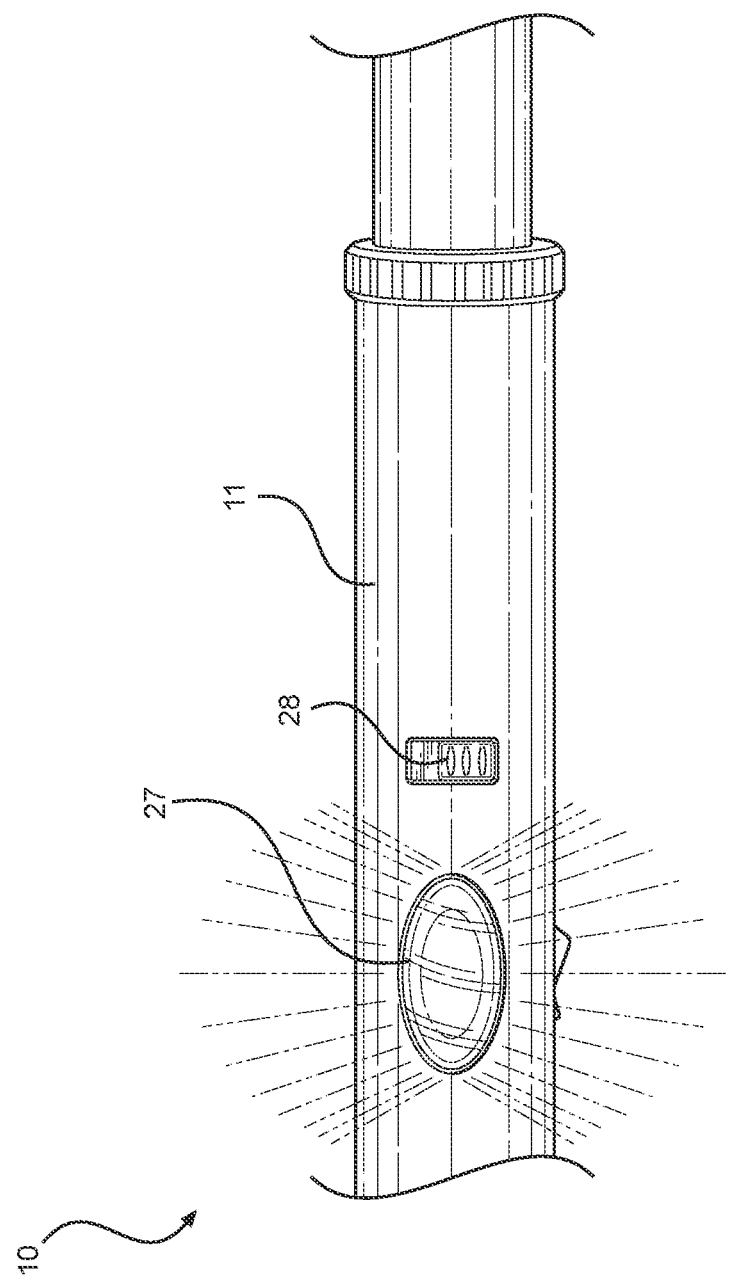
FIG. 4 shows a close-up view of a rear surface of an embodiment of the diaper changing assistance device.

Referring now to FIG. 4, there is shown a close-up view of a rear surface of an embodiment of the diaper changing assistance device. In one embodiment, the diaper changing assistance device 10 further comprises a light 27. The light 27 is disposed on an external surface of the elongated rod 11. The light 27 is operably connected to a power source. Furthermore, the light 27 is operably connected to a light switch 28. The light switch 28 is disposed on the external surface of the elongated rod 11. The light 27 is configured to provide convenience to the user wherein the user is using the diaper changing assistance device 10 in an environment lacking an ideal light source.

Figure 5:
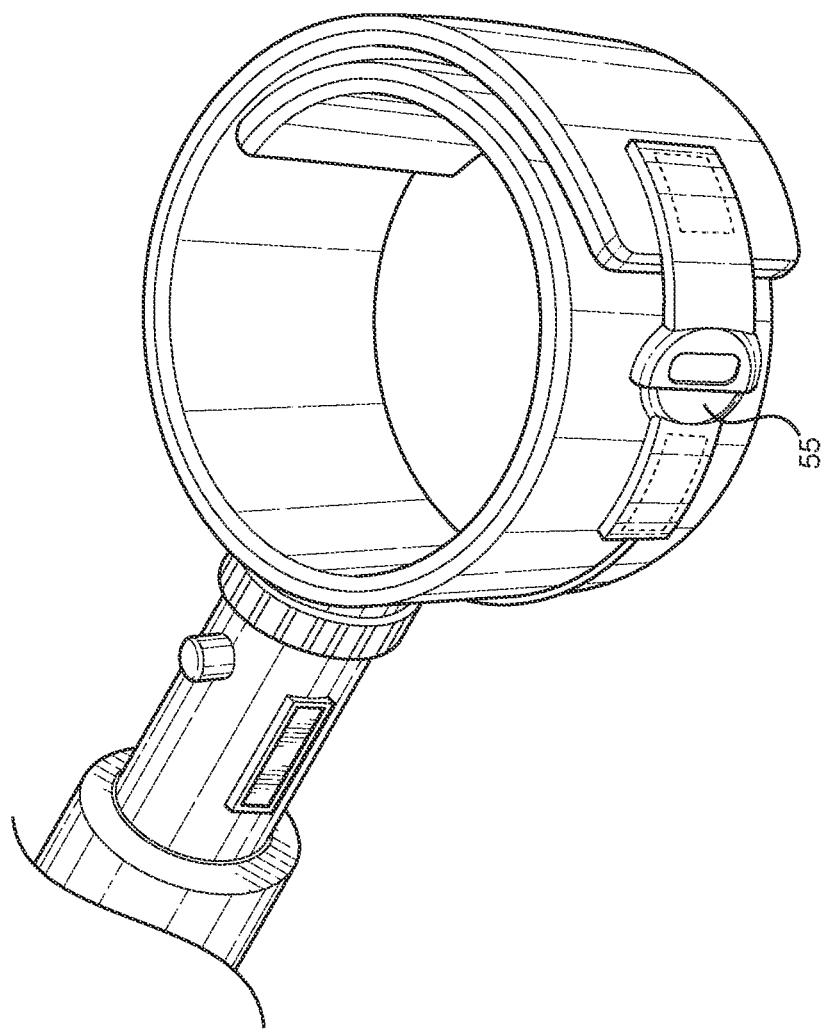
FIG. 5 shows a close-up view of the second end of an embodiment of the diaper changing assistance device.

Referring now to FIG. 5, there is shown a close-up view of the second end of an embodiment of the diaper changing assistance device. In one embodiment, the fastener comprises a pair of snap clasp fasteners 55. The use of snap clasp fasteners 55 is configured to provide ease of use to the user wherein the user is attaching the device to the infant. In another embodiment, the pair of snap clasp fasteners 55 are operably connected to a quick release switch. When the quick release switch is engaged, the pair of snap clasp fasteners 55 are configured to release. It may be desirable for the user to use this embodiment wherein the user wishes to enable quick release of the device from the infant.

Figure 6:
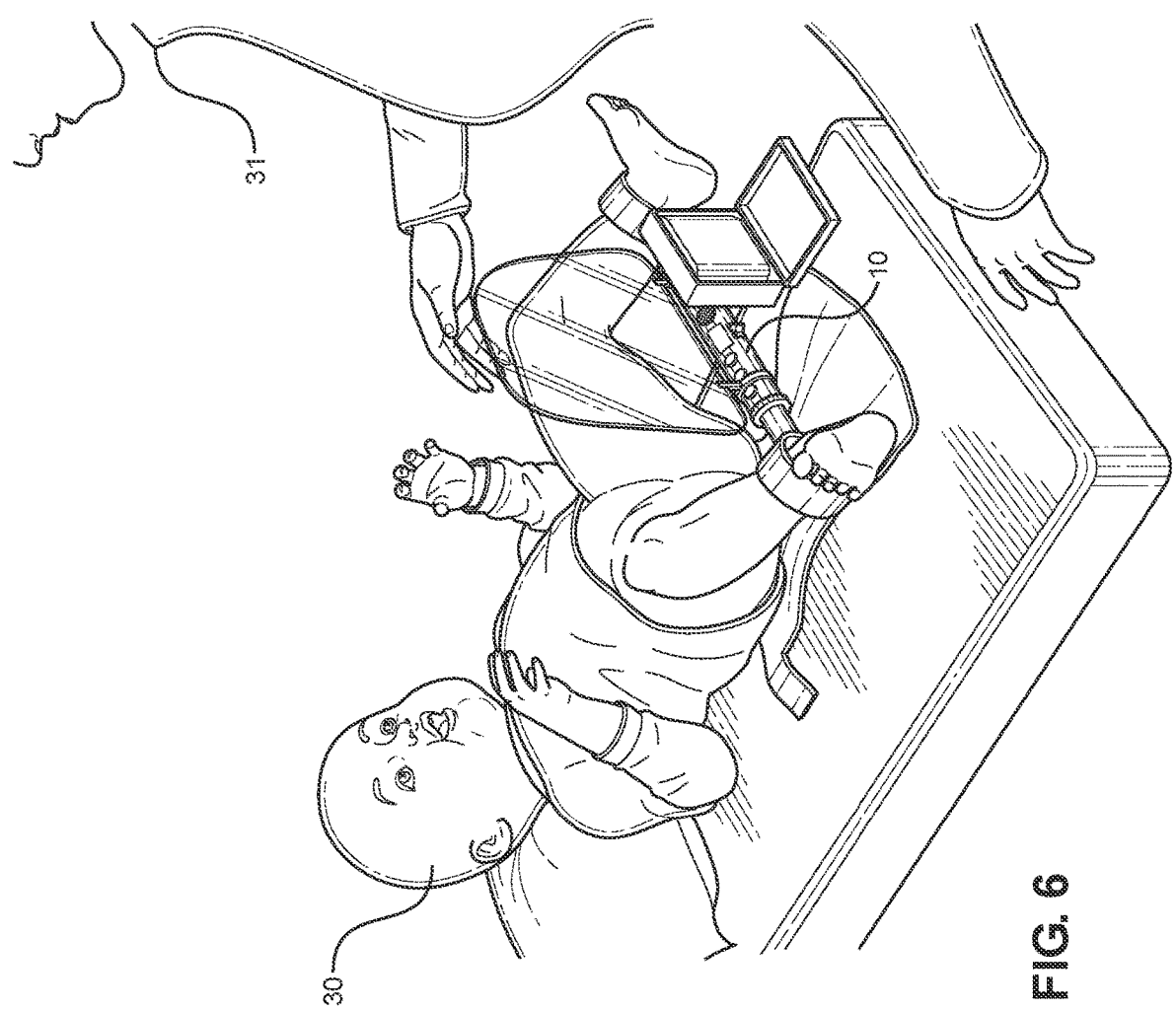
FIG. 6 shows an in use view of an embodiment of the diaper changing assistance device.

Referring now to FIG. 6, there is shown an in use view of an embodiment of the diaper changing assistance device. In use, the diaper changing assistance device 10 is configured to attach to the ankles of an infant 30. The user 31 will then be more easily enabled to lift the leg of the infant 30 upward to change a diaper of the infant 30.

It is therefore submitted that the instant invention has been shown and described in various embodiments. It is recognized, however, that departures may be made within the scope of the invention and that obvious modifications will occur to a person skilled in the art. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A diaper changing assistance device, comprising:
    an elongated rod having a first ringed member disposed at a first end and a second ringed member disposed at a second end;
    wherein each of said first and second ringed members forms a channel configured to receive an ankle in a closed configuration;
    a fastener configured to selectively secure each ringed member about the ankle;
    wherein each of said first and second ringed members is rotatably secured to the elongated rod, wherein each channel extends perpendicular to the elongated rod regardless of rotation thereof;
    wherein the elongated rod is rigid and dimensioned to keep each of said first and second ringed members at a distance therebetween;
    a housing defining a cavity therein;
    wherein a wall of the housing comprises a clip configured to removably attach to the elongated rod;
    the housing having a hingeably movable cover adapted to provide an access point to the cavity.

2. The diaper changing assistance device of claim 1, further comprising an audio mechanism, the audio mechanism comprises:
    a speaker;
    a control switch operably connected to the speaker, wherein activation of the control switch activates the speaker.

3. The diaper changing assistance device of claim 2, wherein a plurality of decorative lights is operably connected to the audio mechanism speaker, such that the decorative lights will flash when the speaker is activated.

4. The diaper changing assistance device of claim 1, wherein the fastener is a pair of snap clasp fasteners.

5. The diaper changing assistance device of claim 4, further comprising a quick release switch disposed on an external surface of the elongated rod wherein the quick release switch is configured to quickly release the snap clasp fasteners.

6. The diaper changing assistance device of claim 1, further comprising:
    a transparent planar member removably attached to the elongated rod.

7. The diaper changing assistance device of claim 6, wherein the housing is disposed entirely between a pair of connectors of the transparent planar member.

8. The diaper changing assistance device of claim 1, further comprising a transparent planar member configured to attach to the elongated rod via a connector.

9. The diaper changing assistance device of claim 1, wherein the elongated rod comprises a first rod member and a second rod member wherein the second rod member is slidably inserted into the first rod member and the second rod member comprises a tab corresponding to a plurality of apertures in the first member wherein the elongated rod is adjustable in length by the movement of the second rod member in the first rod member.

10. The diaper changing assistance device of claim 1, further comprising a light mechanism disposed on an external surface of the elongated rod operably connected to a light switch disposed on the external surface of the elongated rod.

11. The diaper changing assistance device of claim 1, wherein a padding material is disposed on an interior surface of each of said first and second ringed members.

12. The diaper changing assistance device of claim 1, wherein the fastener is a pair of hook and loop fasteners.

13. The diaper changing assistance device of claim 1, further comprising a plurality of decorative lights disposed on an external surface of the elongated rod.

* * * * *